United States Patent [19]

Cobb

[11] Patent Number: 4,510,337

[45] Date of Patent: Apr. 9, 1985

[54] PROCESS FOR PRODUCTION OF 1,1-DIMETHYL-6-HYDROXYINDANS

[75] Inventor: Raymond L. Cobb, Bartlesville, Okla.

[73] Assignee: Phillips Petroleum Company, Bartlesville, Okla.

[21] Appl. No.: 575,593

[22] Filed: Jan. 31, 1984

[51] Int. Cl.³ .................................. C07C 39/12
[52] U.S. Cl. ....................................... 568/734
[58] Field of Search ............................. 568/734

[56] References Cited

U.S. PATENT DOCUMENTS

| | | | |
|---|---|---|---|
| 2,544,815 | 3/1951 | Weaver | 37/98 |
| 3,057,929 | 10/1962 | Arrigo | 568/734 |
| 3,152,192 | 10/1964 | Wood et al. | 568/734 |
| 3,597,472 | 8/1971 | Heiss et al. | 568/734 |
| 3,629,337 | 12/1971 | Degginger et al. | 568/734 |
| 3,954,889 | 5/1976 | Klein et al. | 568/734 |
| 4,107,324 | 8/1978 | Grotkopp et al. | 568/734 |

*Primary Examiner*—Werren B. Lone

[57] ABSTRACT

In the production of 1,1-dimethyl-6-hydroxyindans through the reaction of phenols with isoprene or 2,3-dimethyl-1,3-butadiene in the presence of phosphoric acid, an improvement is comprised of using a phosphoric acid concentration of about 100% instead of 85% or less and also of the distillation of the product mixture from a solution containing phosphoric acid of about 95% concentration.

8 Claims, No Drawings

PROCESS FOR PRODUCTION OF 1,1-DIMETHYL-6-HYDROXYINDANS

This invention relates to the production of 1,1-dimethyl-6-hydroxyindans.

It is known that 1,1-dimethyl-6-hydroxyindans can be prepared by the reaction of a diene with a phenol in the presence of phosphoric acid. However, such processes as heretofore practiced have resulted in limited productivity and in general produced undesirable by-products. Thus, a reaction system which would provide an increased production with a reduction in the undesirable by-products would represent a significant contribution to the art.

Accordingly, it is an object of this invention to provide an improved process for the production of 1,1-dimethyl-6-hydroxyindans.

Other aspects, objects and the several advantages of this invention will be apparent from the specification and appended claims.

In accordance with one embodiment of the present invention, I have discovered that use of 100% $H_3PO_4$ as the condensing catalyst in the preparation of 1,1-dimethyl-6-hydroxyindans through the reaction of a phenol with a diene as hereinafter defined results in an increase in yield of the desired product.

In accordance with another embodiment of this invention, I have discovered further that distillation from phosphoric acid having a concentration of 85 to 100%, preferably 90 to 95%, of the reaction product of a phenol and a diene such as isoprene carried out in the presence of a phosphoric acid condensing agent following washing of the reaction product results in the recovery of more of the desired indane product with less heavies present in the system.

In a still further embodiment of this invention, there is provided an improved process for the preparation of compounds of the formula

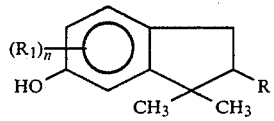

wherein R is a member selected from H and $CH_3$ and $R_1$ is a member selected from alkyl radicals containing up to 5 carbon atoms and n is 0 or an integer of 1 or 2 which comprises:

(A) reacting a phenol of the formula

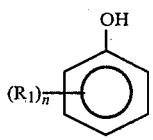

wherein in $R_1$ and n are as above defined with a diene of the formula

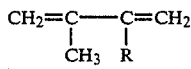

wherein R is as above defined in the presence of phosphoric acid having a concentration in the range of from 85 to 100% at a temperature within the range of from about 25° to 175° C.;

(B) separating the resulting reaction product of Step (A);

(C) admixing the separated indane containing product with phosphoric acid having a concentration in the range of 85 to 100%; and (D) thereafter recovering the desired indane by distillation of the mixture of Step (C) at a temperature in the range of 150° to 220° C.

The term "100% $H_3PO_4$" as used herein means a liquid acid consisting essentially of $H_3PO_4$. Such a liquid is generally prepared by addition of $P_2O_5$ to commercially available $H_3PO_4$ (generally 85% $H_3PO_4$) in an amount sufficient to convert any water present to $H_3PO_4$. In general, the resulting liquid will consist of $H_3PO_4$ in the range of 99 to 100 percent concentration.

Phenols which may be used in accordance with this invention are those of the formula

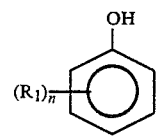

wherein $R_1$ is an alkyl radical containing 1 to 5 carbon atoms. The para position and at least one meta position must be unsubstituted and n is 0 or an integer of 1 or 2.

Examples of suitable phenols are phenol, o-cresol, m-cresol, o-ethylphenol, m-ethylphenol, o-cumenol, m-hydroxycumene, m-propylphenol, o-propylphenol, 2,3-dimethylphenol, 2,5-dimethylphenol, and the like.

The diene reactants which are useful in the present invention are those of the formula

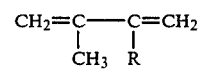

wherein R is hydrogen or methyl.

In carrying out the process of this invention, the diene is added slowly to a stirred mixture of phenol in phosphoric acid. Such acid can be of a concentration of 85 to 100% or in a presently preferred embodiment of the invention 100% $H_3PO_4$. The reaction temperature is maintained at a temperature in the range of 25° to 175° C., preferably 100° to 145° C., during the addition of the diene and stirring is generally continued at the same temperature for up to 2 hours.

After the reaction is completed, the acid is separated and the remaining reaction product may be water washed and thereafter distilled from phosphoric acid having a concentration in the range of 85 to 100%, preferably 90 to 95%. The amount of phosphoric acid added to the distillation pot is preferably in the range of 1 to 20% by weight based on the weight of the phenol and diene used. The temperature in the distillation pot is maintained preferably in the range of 170° to 240° C., which is achieved by gradually reducing the pressure from about 100 torr to about 5 torr during the distillation process.

Also, in carrying out the condensation reaction step of this invention, the proportions of phenol and diene reactants may be varied over wide limits. It is preferred to use somewhat less than one mole of diene per mole of phenol, because of polyalkylation, preferably 0.6 to 0.9 mole of diene per mole of the phenol.

The phosphoric acid catalyst may be employed in amounts varying from about 5 to 200%, preferably 20 to 40% by weight, based on the phenol employed.

The temperature at which the condensation step of this invention is carried out is preferably in the range of 100° C. to 145° C.

The hydroxy substituted indans prepared by the process of this invention are useful as antioxidants for organic materials which are normally subject to oxidative deterioration such as rubber. In addition, such compounds are suitable for use as intermediates in the preparation of indan-5-yl-N-methyl carbamic acid esters which have arthropodicidal and fungicidal properties.

The invention is further illustrated by the following examples. Temperatures given in the specification are in degrees centigrade.

EXAMPLE 1

Phenol (50 grams) (0.53 mol), 100 mL of xylene and 20 mL of 85% $H_3PO_4$ were mixed and heated to 110° C. A total of 40 mL of isoprene (0.38 mol) was added over a 30 minute interval while heating and stirring were continued. Samples taken at 1 hour intervals indicate that the reaction was essentially complete in 1 hour. However, for consistency, the results reported are those taken at the end of 3 hours reaction time since the preparations using the lower concentrations of phosphoric acid show some linear precursors present even after 3 hours reaction time.

GLC analysis on small samples that had been washed with water to remove the acid showed that with a 93% conversion of the phenol, there was a 31% selectivity to 1,1-dimethyl-6-hydroxyindane (DMHI) and 35% to 2,2-dimethylbenzopyran (DMBP).

EXAMPLE 2

The procedure of Example 1 was followed except that 15.0 grams of $P_2O_5$ was added with the 20 mL of 85% $H_3PO_4$ in the xylene before the addition of the isoprene.

GLC analysis showed that with an 89% conversion of the phenol, a 45% selectivity to DMHI and a 30% selectivity to DMBP were obtained.

This run which indicates the improvement in the yield of the desired dimethylhydroxyindane realized through the use of the more concentrated phosphoric acid is included as Run 9 in Table I along with other runs.

EXAMPLE 3

A further series of runs were carried out at 110° C. and 135° C. using the procedure of Example 1 except that the concentration of the phosphoric acid was varied. Samples were taken at 4 hours reaction time.

The results of this series of runs is set forth in Table I.

TABLE I

| | | | Analyses by G.L.C. | | |
|---|---|---|---|---|---|
| Run No. | Temp., °C. | $H_3PO_4$ Conc. % | Conversion of Phenol % | DMBP (Dimethyl-benzopyran) | DMHI (Dimethyl-hydroxy-indane) |
| 1 | 110 | 72 | 80 | 36 | 46* |
| 2 | 110 | 76 | 82 | 37 | 38* |
| 3 | 110 | 80 | 86 | 38 | 33* |
| 4 | 110 | 85 | 93 | 35 | 31 |
| 5 | 110 | 90 | 92 | 40 | 36 |
| 6 | 110 | 95 | 92 | 34 | 36 |
| 7 | 110 | 98 | 92 | 32 | 39 |
| 8 | 110 | 99.3 | 91 | 35 | 39 |
| 9 | 110 | 100 | 89 | 30 | 45 |
| 10 | 110 | 100 | 84 | 33 | 53 |
| 11 | 135 | 100 | 83 | 28 | 54 |
| 12 | 135 | 100 | 87 | 28 | 53 |
| 13 | 135 | 100 | 81 | 36 | 54 |
| 14 | 135 | 100 | 81 | 24 | 55 |

*Includes alkenylated phenolic precursor.

The above data shows that the yield of the desired DMHI is increased and the yield of the dimethylbenzopyran reduced when the concentration of the phosphoric acid is increased to 100.

EXAMPLE 4

In a further series of runs in which 71% phosphoric acid was used as the catalyst, the reactions were quenched with water and the organic layers were separated, combined, mixed and divided. A 188 gram portion (A) of this mixture was distilled. The distilled products included 6.6 grams of phenol, 58.6 grams of DMHI, 46.8 grams of DMBP, and 44.6 grams of residue. To a second portion of 188 grams (B) was added 5 mL of $H_3PO_4$ and 2 grams of $P_2O_5$ (94% $H_3PO_4$) and the mixture was distilled. From this distillation was obtained 23.4 grams of phenol, 60.0 grams of DMHI, 46.4 grams of DMBP and 22.2 grams of heavies which included the 11 grams of phosphoric acid added. In both cases the numbers shown for DMHI do contain some DMHI precursors. These data do show that more of the unreacted phenol is recovered and less of the residue is formed. These data are tabulated in Run 1 in Table II.

EXAMPLE 5

In a further run, xylene (750 mL), 250 grams of phenol, 20 mL of 85% $H_3PO_4$ and 15 grams of $P_2O_5$, (the equivalent of 51.7 grams of 100% $H_3PO_4$) were heated to 135° C. and 225 mL of isoprene was added over a 2.5 hour interval. The reaction was quenched with water and the organic layer was separated. The product mixture was divided into two approximately equal portions. The first portion of 214 grams (A) was distilled. From this distillation, 8.8 grams of phenol was recovered along with 62.9 grams of DMHI, 46.3 grams of DMBP, and 43.0 grams of residue. To the other portion of 212 grams was added 5 mL of $H_3PO_4$ and 2 grams of $P_2O_5$ (94% $H_3PO_4$) and the mixture was distilled. From this distillation was obtained 19 grams of phenol, 69.4 grams of DMHI, 51.7 grams of DMBP and 20.7 grams of residue including the 11 grams of the phosphoric acid which had been added.

The results of these Examples as shown in Table II demonstrate that both the addition of the 100% phosphoric acid to the reaction mixture and the addition of 94% phosphoric acid to the distillation pot are beneficial. Table II summarizes the data obtained in Examples 4 and 5.

TABLE II

| Run | Charge, Grams | Added to Distillation Pot | Phenol, Unconverted | DMBP[a] (dimethyl-benzopyran) | DMHI[b] (dimethyl-hydroxy indane) | Heavies |
|---|---|---|---|---|---|---|
| 1 | Control Run | | | | | |
| A. | 188 | — | 6.6 | 46.8 | 58.6[c] | 44.6 |
| B. | 188 | 94% $H_3PO_4$ (11 grams) | 23.4 | 46.4 | 60.0[c] | 32.2[d] |
| 2 | Inventive Run & Distillation | | | | | |
| A. | Inventive Run - Reaction run in 100% $H_3PO_4$ | | | | | |
| | 214 | — | 8.8 | 46.3 | 62.9 | 43.0 |
| B. | Inventive Run and Inventive Distillation | | | | | |
| | 212 | 94% $H_3PO_4$ (11 grams) | 19.0 | 51.7 | 69.4 | 30.7[d] |

[a]DMBP = Dimethylbenzopyran.
[b]DMHI = Dimethylhydroxyindane.
[c]Includes acyclic precursors.
[d]Including the $H_3PO_4$ added.

Table III provide additional information on the distillation of DMHI product mixtures with various types of acid additives.

The data show the variation in the amount of pot residue resulting from the variation in the acid added to the distillation pot. A reaction product mixture was divided into several 100 gram samples. One sample was distilled as a control without an acid additive and each of the others were distilled after adding the acid additive indicated.

TABLE III
Effect of Variations in Acid Added to Distillation Pot on the Amount of Distillable Products

| Run | Added to Distillation Charge Additive, | Grams | Distillables Taken Overhead, Grams | Pot Residue*, Grams |
|---|---|---|---|---|
| Composite Reaction Product Mixture A: | | | | |
| Control | — | — | 59.5 | 42.8 |
| 1 | $H_3PO_4$ on kieselguhr | 18 | 67.3 | 43.1 |
| 2 | Filtrol 13** | 6 | 58.2 | 47.3 |
| 3 | 85% $H_3PO_4$ | 9 | 87.5 | 19.4 |
| 4 | 95% $H_3PO_4$ | 9 | 90.5 | 19.8 |
| 5 | $P_2O_5$ | 5 | 60 | 45 |
| Composite Reaction Product Mixture B: | | | | |
| Control | — | — | 74.3 | 26.3 |
| 1 | 95% $H_3PO_4$ | 11 | 90.1 | 21.8 |
| 2 | 100% $H_3PO_4$ | 15 | 86.1 | 29.2 |
| 3 | $P_2O_5$ | 5 | 75.3 | 29.4 |

*Pot residues include acid additive where applicable.
**Acid treated clay.

These data show that it is advantageous to have phosphoric acid present in the distillation pot during distillation and that it is most advantageous to use an acid of 100% concentration.

The foregoing illustrates the invention, which, however, is not to be limited thereby, but is to be construed as broadly as permissible in view of the prior art and limited solely by the appended claims.

I claim:

1. A process for preparing compounds of the formula

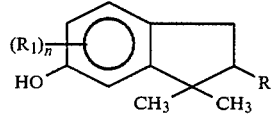

wherein R is a member selected from H and $CH_3$ and $R_1$ is a member selected from alkyl radicals containing up to 5 carbon atoms and n is 0 or an integer of 1 or 2 which comprises:

(A) reacting a phenol of the formula

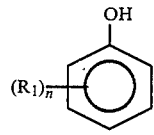

wherein in $R_1$ and n are as above defined with a diene of the formula

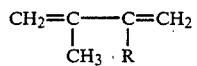

wherein R is as above defined in the presence of first phosphoric acid having a concentration in the range of from 85 to 100% at a temperature within the range of from about 25° to 175° C.;

(B) separating the resulting reaction product of Step (A);

(C) admixing the separated indane containing product with a second phosphoric acid having a concentration in the range of 85 to 100%; and (D) thereafter recovering the desired indane by distillation of the mixture of Step (C) at a temperature in the range of 150° to 220° C.

2. A process according to claim 1 wherein the phosphoric acid of Step A is of a concentration of 85% and the phosphoric acid of Step C is of a concentration of 100%.

3. A process according to claim 2 wherein said phenol compound is phenol and said diolefin is isoprene.

4. A process according to claim 1 wherein said first phosphoric acid is 100% phosphoric acid and said second phosphoric acid is 94% phosphoric acid.

5. A process according to claim 4 wherein said phenol compound is phenol and said diolefin is isoprene.

6. A process according to claim 1 wherein the molar ratio of diene to phenol is in the range of 0.6 to 0.9.

7. A process for preparing

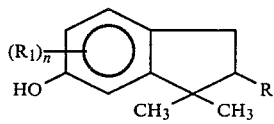

wherein R is a member selected from H and CH$_3$ and R$_1$ is a member selected from alkyl radicals containing up to 5 carbon atoms and n is 0 or an integer of 1 to 2 which comprises:

(A) reacting a phenol of the formula

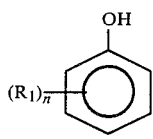

wherein R$_1$ and n are as above defined with a diene of the formula

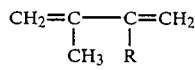

wherein R is as above defined in the presence of phosphoric acid having a concentration of about 100% at a temperature within the range of 25° to 175° C.

8. In a process for the recovery of an indane of the formula

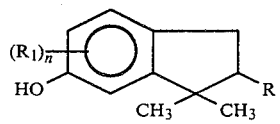

which has been prepared by the reaction of a phenol of the formula

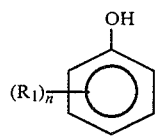

wherein R$_1$ is a member selected from alkyl radicals having up to 5 carbon atoms and n is an integer of 1 or 2 with a diene of the formula

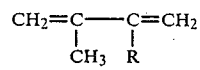

wherein R is a member selected from H and CH$_3$, the improvement which comprises admixing the resulting indane product with a phosphoric acid having a concentration in the range of 85 to 100% and thereafter distilling the resulting mixture from phosphoric acid having a concentration in the range of 85 to 100%.

* * * * *